United States Patent
Gershowitz

(10) Patent No.: US 7,588,723 B2
(45) Date of Patent: Sep. 15, 2009

(54) AIR REMOVAL DEVICE WITH FLOAT VALVE FOR BLOOD PERFUSION SYSTEM

(75) Inventor: Arthur D. Gershowitz, Ann Arbor, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 848 days.

(21) Appl. No.: 11/118,726

(22) Filed: Apr. 29, 2005

(65) Prior Publication Data

US 2005/0261618 A1    Nov. 24, 2005

Related U.S. Application Data

(60) Provisional application No. 60/573,923, filed on May 24, 2004.

(51) Int. Cl.
*A61M 1/00* (2006.01)
*A61M 37/00* (2006.01)

(52) U.S. Cl. .................. 422/44; 604/4.01; 604/6.15; 604/320

(58) Field of Classification Search ............ 422/44–48; 604/8–10, 4.01, 403–411, 5.01, 6.01–6.16, 604/151–153, 246, 249, 317–322, 327; 137/15.26; 210/247, 304, 315, 446; 128/DIG. 3, DIG. 24
See application file for complete search history.

(56) References Cited

U.S. PATENT DOCUMENTS

| | | | | |
|---|---|---|---|---|
| 3,849,071 A | * | 11/1974 | Kayser | 422/45 |
| 4,599,093 A | * | 7/1986 | Steg, Jr. | 95/46 |
| 4,708,157 A | * | 11/1987 | Sabatino | 137/179 |
| 5,824,212 A | * | 10/1998 | Brockhoff | 210/194 |
| 5,935,105 A | | 8/1999 | Manning et al. | |
| 6,248,231 B1 | | 6/2001 | Di Bella et al. | |
| 6,267,926 B1 | * | 7/2001 | Reed et al. | 422/48 |
| 6,337,049 B1 | * | 1/2002 | Tamari | 422/44 |
| 6,517,732 B1 | | 2/2003 | Brockoff et al. | |
| 2001/0010802 A1 | | 8/2001 | Tamari | |
| 2004/0009097 A1 | | 1/2004 | Stringer et al. | |
| 2004/0197223 A1 | | 10/2004 | Olsen et al. | |

OTHER PUBLICATIONS

Medtronic, *Resting Heart™ Module*, 2003.

* cited by examiner

*Primary Examiner*—Tatyana Zalukaeva
*Assistant Examiner*—Philip R Wiest
(74) *Attorney, Agent, or Firm*—Gael Diane Tisack, Esq.; MacMillan, Sobanski & Todd, LLC

(57) ABSTRACT

An input blood supply within a blood perfusion system is pumped through a chamber. A centrifugal flow of the input blood supply is formed in a bottom region of the chamber to cause air to migrate toward an axial center of the chamber. A float is buoyantly suspended on the centrifugal flow wherein the float is disposed for vertical movement in the chamber, and wherein the float has an effective density less than the density of the blood. When a volume of air present within the chamber is less than a predetermined volume, then the float closes a valve at an air outlet from the chamber. When a volume of air present within the chamber is greater than the predetermined volume, then the float opens the valve to remove air from the chamber.

23 Claims, 7 Drawing Sheets

AIR REMOVAL DEVICE WITH FLOAT VALVE FOR BLOOD PERFUSION SYSTEM

CROSS REFERENCE TO RELATED APPLICATIONS

This application claims priority to U.S. provisional application Ser. No. 60/573,923, filed May 24, 2004.

STATEMENT REGARDING FEDERALLY SPONSORED RESEARCH

Not Applicable.

BACKGROUND OF THE INVENTION

The present invention relates in general to extracorporeal blood perfusion systems, and, more specifically, to an air removal device for separating entrained air from blood flowing in the system.

When heart surgery is performed 'on pump', steps are taken to remove air entrained in the blood flowing in the extracorporeal blood circuit. Preferably, air removal occurs upstream of the pump. Typically, either a cardiotomy reservoir with defoamer or a flexible venous reservoir (FVR) has been employed. An FVR typically comprises a sealed bag with a luer valve or stopcock at its upper end for manually removing excess air. A cardiotomy reservoir comprises a hard shell for collecting and storing blood which is then supplied to the pumped system. The collection chamber is open to atmosphere and the blood is at atmospheric pressure. Any air bubbles in the blood rise to the top of the collection chamber. Blood is resident in the reservoir for a time that is sufficiently long for air to separate. A blood defoamer is often mounted in the reservoir to aid in the breakdown of foam bubbles in the chamber. Substantially bubble-free blood is drawn out of the reservoir at the bottom. The cardiotomy reservoir can also be used for filtration of particulates or for addition of fluids or pharmacological agents.

Blood from a patient can be collected passively or actively. Passive drainage is accomplished by catheterizing the patient, connecting the catheter with tubing to a cardiotomy or FVR, and siphoning the blood into the cardiotomy or FVR. Active drainage is accomplished by using either a pump or vacuum source on the drainage line to pump or suction blood from the access site. The resulting blood flow rate is greater than what is obtained using passive drainage. When drainage is passive, the pressure in the extracorporeal circuit upstream of the blood pump typically becomes slightly positive relative to atmospheric. When drainage is active, the pressure in the circuit upstream of the pump frequently becomes less then atmospheric. Either a cardiotomy or FVR may be used when drainage is passive. An FVR will not work during active drainage because the negative pressure in the circuit will cause the FVR to collapse.

Certain advantages could be realized by eliminating the use of the cardiotomy reservoir. For instance, a reduction in blood contacting surface areas, a reduction of blood to air interface, a reduction of fluid priming volume of the perfusion circuit, and elimination or reduction of the amount of blood-to-defoamer contact are all expected to improve patient outcome. Since an FVR provides a closed system (i.e., not open to atmosphere) it can achieve some of these advantages to a certain degree, but it cannot be used when active drainage is desired because of the tendency to collapse under negative pressure.

Hard shell reservoirs have been used in a closed configuration in order to implement vacuum-assisted blood collection from the patient (i.e., systems known as VAVD for Vacuum Assisted Venous Drainage). The large reservoirs require a large volume of blood and generate a large blood to air interface and often use defoamer in the flow path to prevent air bubbles leaving the reservoir. In a VAVD reservoir, the blood path is continuously connected to and at the same pressure as the vacuum source. They require monitoring by the perfusionist to maintain a stable level in the reservoir by balancing blood inflow and outflow. Also known are kinetic-assist devices using a smaller chamber wherein suction for collecting blood from the patient is directly obtained from a blood pump. However, these systems require an active electronic sensor such as an ultrasonic sensor for detecting the presence of collected air and an electronically-controlled purge valve that is triggered when air is sensed. Cost and potential reliability issues associated with active sensing and purging are disadvantageous. It would be advantageous to be able to remove significant quantities of air from blood flowing at high flow rates in a passive manner (i.e., without either electronic sensors or requiring a balancing of inflow and outflow rates) and doing so whether the pressure within the system is higher or lower than atmospheric pressure.

SUMMARY OF THE INVENTION

The present invention provides an air removal device and method with low prime volume, efficient air removal, and minimal exposure of blood to a defoamer. The device described herein does not collapse under negative pressure and can be used in place of a cardiotomy reservoir for both passive and active drainage procedures.

In one aspect of the invention, an air removal device is provided for removing air from blood flowing in a perfusion system. A chamber has a blood flow region at a lower end thereof and an air collection region at an upper end thereof. The chamber further has an inlet, a blood outlet, and an air outlet vertically higher than the inlet, wherein the air outlet includes an outlet mating surface proximate to an exit passage. A float is disposed for vertical movement in the chamber, wherein the float has an effective density less than the density of blood, and wherein the float includes a sealing surface for engaging the outlet mating surface and blocking the exit passage when the float is at its vertically highest position.

DETAILED DESCRIPTION OF PREFERRED EMBODIMENTS

Figure 1:
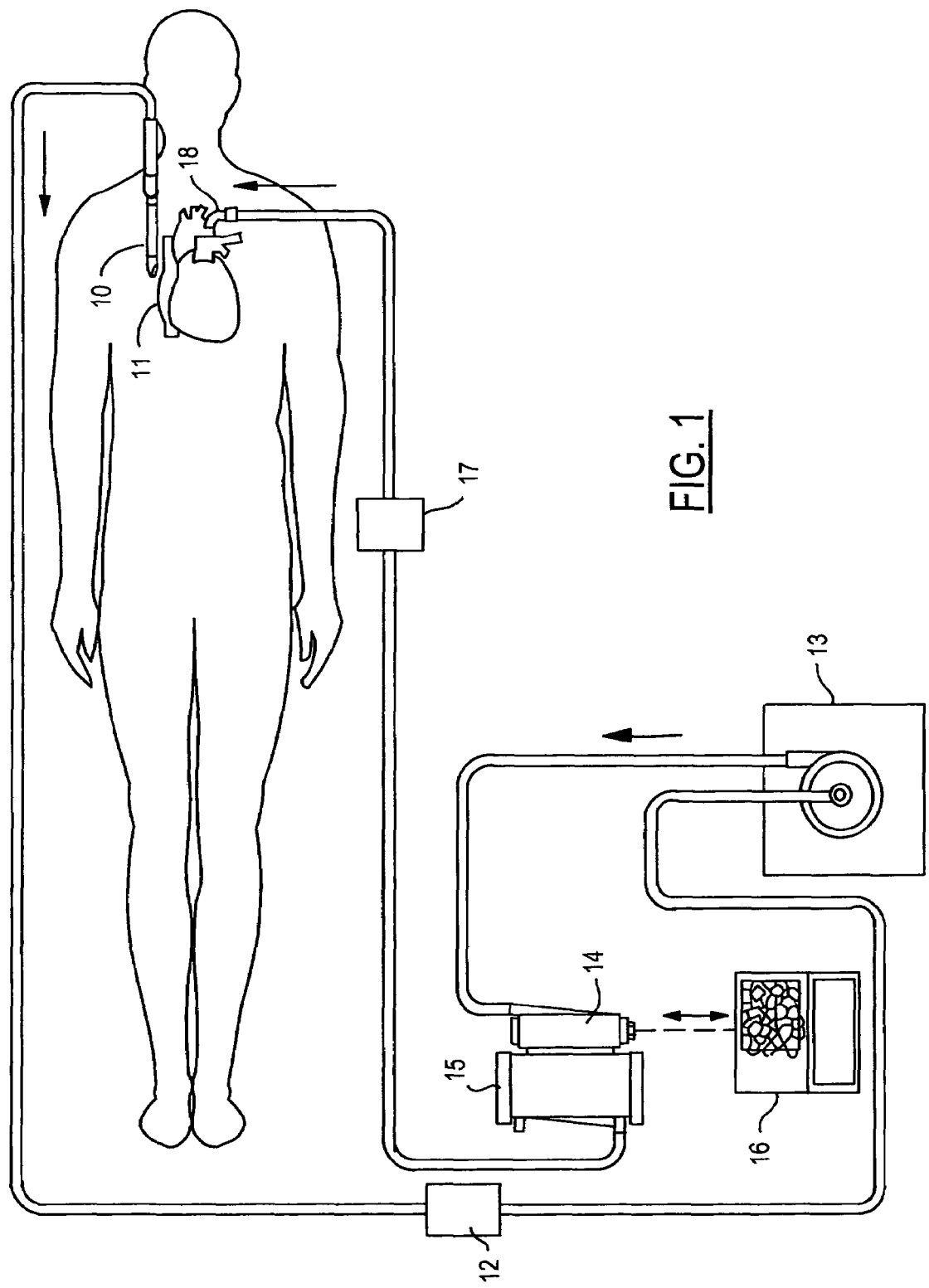
FIG. 1 is a diagrammatic view of a perfusion system of the present invention.

FIG. 1 shows a simplified diagram of a perfusion system for supporting on-pump coronary artery bypass graft surgery. A venous catheter 10 is inserted at 11 into the right side of a patient's heart or the superior or inferior vena cava. Venous blood flow is driven by an arterial pump 13 which may be comprised of a centrifugal pump, for example. Blood passes through a heat exchanger 14 and then to an oxygenator 15. A blood heater/cooler 16 is connected to heat exchanger at 14 for selectably heating or cooling blood as is required during different phases of surgery. Oxygenated blood is conducted to an arterial cannula 18 to return the oxygenated blood to the patient's aorta.

Air in the form of a bolus or bubbles can be introduced into the blood at the point of extraction from the body due to a leak around the venous catheter, for example. It is desirable to remove entrained air prior to the blood entering the oxygenator. Thus, an air removal device 12 is preferably inserted into the venous line. Rather than or in addition to air removal device 12, an air removal device 17 may be used in the arterial side of the circuit.

Figure 2:
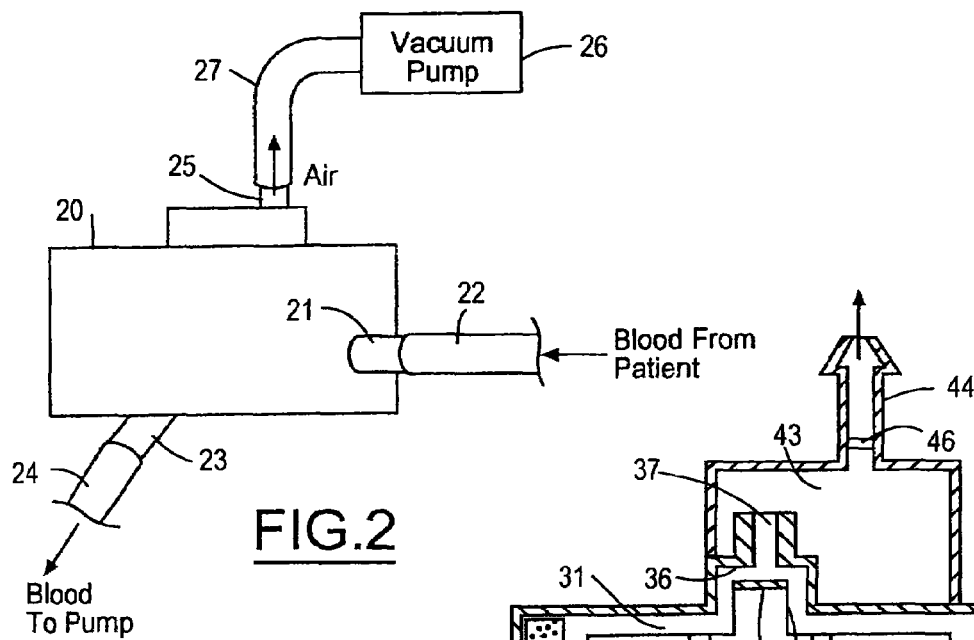
FIG. 2 is a diagrammatic view of an air removal device of the present invention.

Among other objectives, the present invention seeks to minimize prime volume of the perfusion circuit as well as reducing surface area of blood contact and the exposure of blood to air (the air/blood interface). It is further desirable to handle large volumes of both air and blood while removing large amounts of air in a short period of time while using a device that does not collapse when the circuit pressure is below atmospheric pressure. FIG. 2 shows an air separator device 20 having an inlet 21 connected to a flow line 22 for receiving a blood/air mixture from the patient and a blood outlet 23 connected via a flow line 24 to an arterial pump. An air outlet 25 is connected to a vacuum pump 26 via an air removal line 27. Device 20 preferably uses a rigid body for withstanding negative pressure present in an active system.

Figure 3:
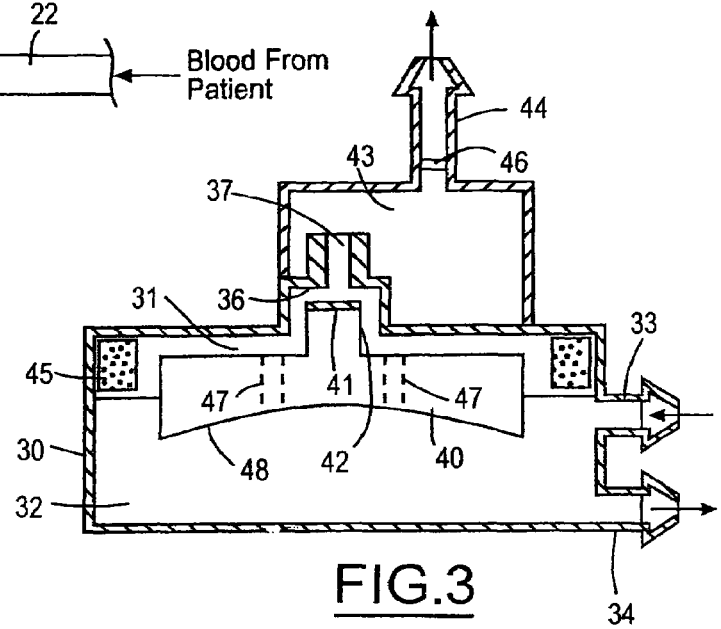
FIG. 3 is a cross-sectional view of a first embodiment of an air removal device.

FIG. 3 is a schematic, cross-sectional view illustrating the main functional elements of the present invention. A main chamber 30 comprises a rigid housing with a cylindrical interior space that has an upper air collection region 31 and a lower blood flow region 32. An inlet 33 and an outlet 34 preferably provide a tangential flow into and out of chamber 30 in order to create a spiral flow path. Preferably, inlet 33 is vertically higher than outlet 34. An air outlet 35 from chamber 30 is vertically higher than inlet 33. Outlet 35 has an outlet mating surface 36 and an exit passage 37.

A float 40 is disposed for vertical movement in chamber 30. In order to float on blood passing through the device, float 40 has an effective density (i.e., weight divided by total displacement volume) less than the density of blood. It includes a sealing surface 41 that may be disposed at the end of a stem 42 in order to selectably engage outlet mating surface 36. Thus, exit passage 37 is blocked when float 40 is at its vertically highest position (i.e., when the blood level within chamber 30 is at a desired maximum height). Chamber 30 and float 40 are constructed of biocompatible materials such as polycarbonates, polypropylene, or other biologically inert materials as is known in the art.

The centrifugal blood flow within chamber 30 created by the tangential input causes air within the blood to migrate toward the central vertical axis of chamber 30. Air buoyancy causes it to further migrate upward to the air collection region. Other features such as spirally-shaped guide channels within the blood flow chamber can also be used to enhance centrifugal separation of blood and air. Only the area of the blood flow region in this embodiment needs to be cylindrical. The chamber surrounding the air collection region could be square or any other shape since it does not utilize a centrifugal flow of air. When the volume of air (e.g., from separated bubbles) within chamber 30 increases, the volume of blood in the device decreases and float 40 moves down from its vertically highest position. In consequence, the valve formed by mating surface 36 and sealing surface 41 opens and allows collected air to escape via an overflow chamber 43 to a vacuum port 44 which is preferably connected to a vacuum pump as shown in FIG. 2.

In order to assist in the breakup of bubbles within air collection region 31, a blood defoamer 45 of the type conventionally used in a cardiotomy is mounted at the upper end of chamber 30. In the event that any small amounts of blood or blood foam pass through exit passage 37, such blood is collected in overflow chamber 43 and prevented from moving through vacuum port 44 by an optional hydrophobic membrane 46.

So that float 40 does not impede the flow of air being collected, internal passageways 47 may be provided. Furthermore, float 40 preferably includes a sloped bottom 48 to prevent air accumulation beneath the float. Sloped bottom surface 48 is shown as being concave for guiding air bubbles toward passages 47. Alternatively, a convex surface or any continuous slopes that avoid air collection areas can be used. A flat bottom can be used, however, a greater float weight may be needed due to additional buoyancy in the presence of blood foam.

The rigid chamber of the present invention permits the air removal device to achieve passive removal of air from the chamber even when pressure in the blood flow circuit is less than atmospheric pressure. Since it is a mechanically operated device, only the connection to a vacuum source (or maintaining a system pressure greater than atmospheric) is required in order to operate properly. The arrangement of the float and the valve components insures that the sealing surface of the float will contact and seal the air exit passage before the blood level approaches the outlet. This prevents blood from being sucked back into the vacuum line as air is being drawn out of the chamber. Therefore, a small amount of residual air is maintained at the top of the chamber even after the float seals the outlet. Once the outlet is sealed, the float is held against the outlet by both the buoyancy exerted by the blood and the suction applied by the vacuum.

For proper operation, the weight of the float must exceed the suction force exerted by the vacuum so that the weight of the float causes it to disengage from the mating surface as the blood level drops. A buoyant force is exerted on the float that depends on 1) the weight of blood that the float is displacing and 2) support of the float by any blood foam that may be present beneath it. Thus, the weight of the float must also overcome the buoyancy of the float floating upon such blood foam. In order to float on the blood itself, the first component of the buoyant force must be equal to or greater than the weight of the float (i.e., the density of the float must be equal to or less than the density of blood). The float weight is chosen between these upper and lower bounds.

The size of exit passage 37 is sufficiently large to allow passage of the required flow rate of air when the valve is open but is sufficiently small to avoid excessive suction force which may prevent the float from dropping off when the blood level drops.

In preparation for surgery, a perfusion circuit is typically connected up and then filled with a priming fluid such as saline. Prior to priming, the chamber of the air removal device is full of air. The vacuum port is connected to a vacuum source in preparation for priming of the circuit. At that time, the float is at its vertically lowest position and the air valve is open. As the chamber begins to fill with priming fluid, the vacuum source continues to draw air out of the chamber and the fluid level rises within the chamber. Eventually, the float is pushed up against the outlet mating surface to close the exit passage and the fluid level stabilizes.

During subsequent flow of blood through the air removal device during surgery, any air introduced into the chamber carried by the blood separates and collects at the top of the chamber. The increased volume of air lowers the blood level, reducing the buoyant force on the float. The float remains against the air outlet as long as the buoyant force and the suction exerted by the vacuum are greater than the weight of the float. As more air is introduced and the blood level continues to drop, the float eventually falls away from the outlet thereby permitting air to be drawn off through the vacuum port and the blood level to again increase until the air valve is again closed.

Sealing surface 41 of float 40 preferably comprises a low durometer material which conforms to outlet mating surface 36. Rather than a separate sheet or disk, if the entire float is made of low durometer material then the float could provide the sealing surface directly. To prevent capillary action between the float and the chamber, a sufficiently large gap or space is provided between the outer edge of the main body portion of the float and the inner edge of the chamber. As shown in FIG. 3, this space may be occupied by a torus of defoamer material 45. Preferably, defoamer to blood contact is minimized by placing the defoamer mostly or entirely above the maximum blood level. The present invention avoids placing defoamer across the flow path of the blood, thereby allowing most of the blood not to contact the defoamer at all.

In order to insure alignment of the sealing surface with the mating surface forming the air valve, guide features may be provided such as a guide passage 49 in chamber 30 for receiving stem 42. Although float 40 is shown as a solid material, it could be hollow (i.e., containing internal air chambers) in order to allow the float to be made out of material denser than blood if desired.

Figure 4:
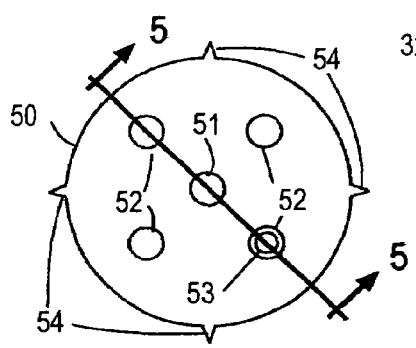
FIG. 4 is a top view of a float body according to one embodiment.

FIG. 4 shows a top view of an alternative float 50 including a central guide stem 51 and vertical air passages 52. A block of defoamer material 53 may be included in one or more air passages 52. In order to guide the vertical movement of float 50 against the chamber, a plurality of reliefs 54 may be provided on the outer periphery of float 50. Reliefs 54 could alternatively be located around the outer periphery of stem 51. In addition to aligning float 50 so that the stem is properly centered for implementing the air valve, the reliefs reduce frictional forces during float movement.

Figure 5:
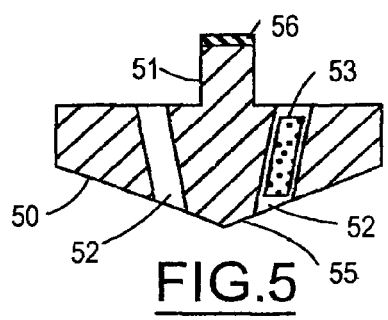
FIG. 5 is a cross-sectional view of the float body along lines 5-5 of FIG. 4.

Float 50 is shown in cross section in FIG. 5. A bottom surface 55 of float 50 is sloped oppositely as compared to float 40 in FIG. 3. Pliant sheet 56 provides a sealing surface for interfacing with an output port as previously described.

Figure 6:
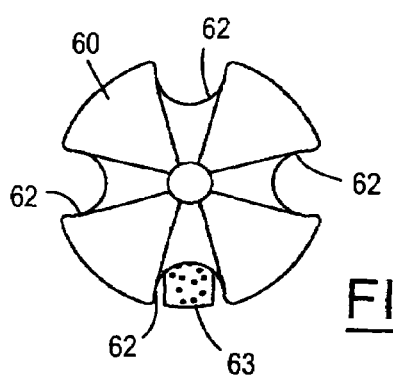
FIG. 6 is a top view of an alternative float body.
Figure 7:
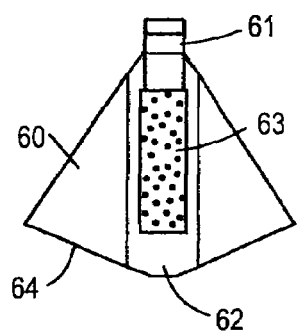
FIG. 7 is a side view of the float body of FIG. 6.

FIG. 6 is a top view of yet another alternative shape for a float 60 which includes a stem 61 and a body including vertical slots 62. A defoamer block 63 is attached to float 60 in one of slots 62. A sloped bottom surface 64 as shown in FIG. 7 and vertical slots 62 provide for easy flow of air toward the air outlet.

A circumferential flow or spiraling flow of blood within the chamber greatly aids in the air separation. Thus, the blood inlet is preferably tangential to the cylindrical blood flow chamber and the blood outlet is preferably at least partially tangential. Alternatively, tangential flow can be achieved by using deflectors within the chamber to redirect flow from a non-tangential inlet or outlet. In general, a chamber with a larger diameter and shorter height is preferable since these achieve a reduction in downward velocity of the combined blood and air bubbles, making it easier for the bubbles to overcome a downward momentum and to escape from the blood.

Figure 8:
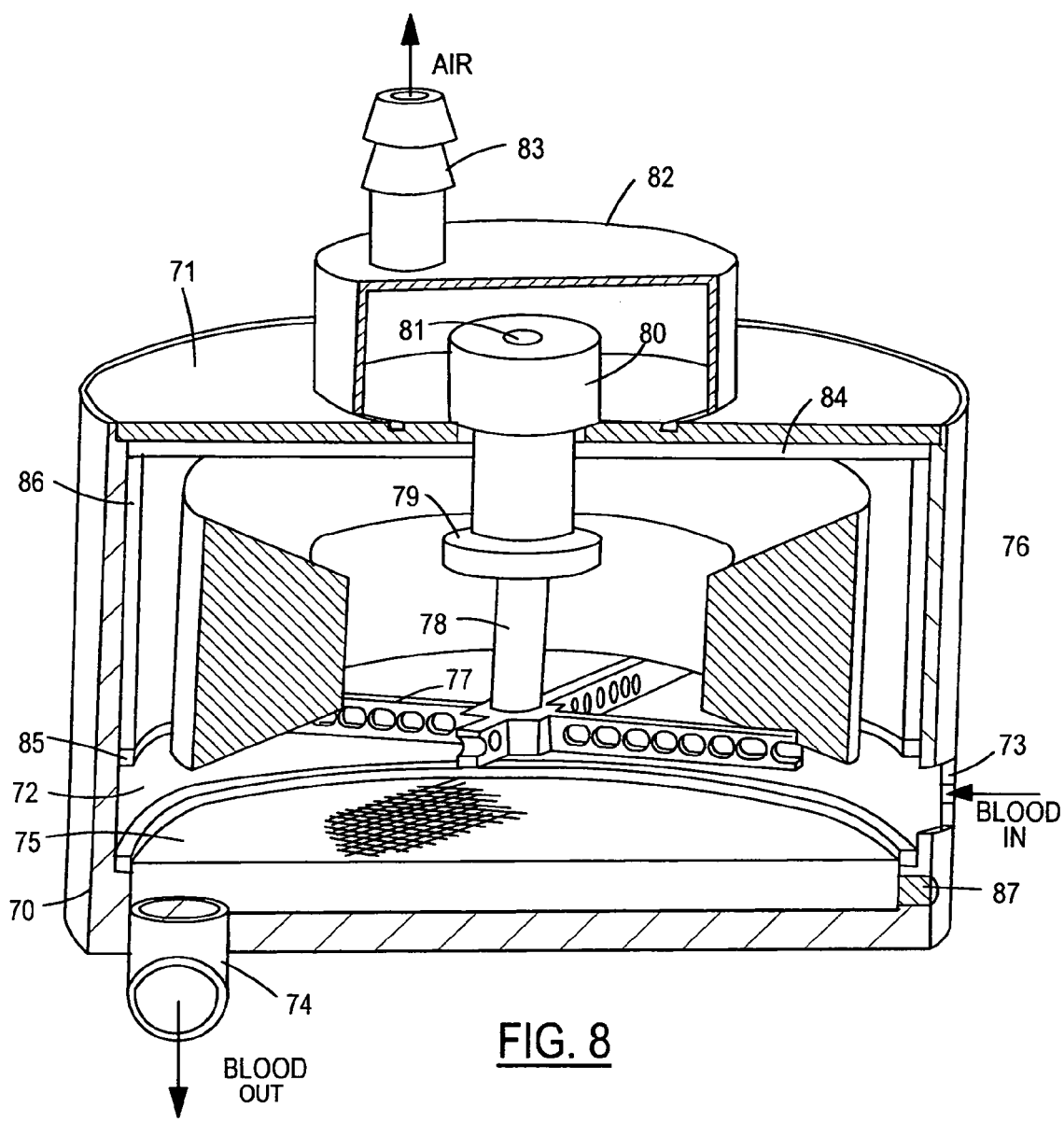
FIG. 8 is a partial cross section, perspective view showing another preferred embodiment of the air removal device of the present invention.

A more detailed embodiment of the air removal device is shown in partial cross-section in FIG. 8. A base member 70 is generally cup-shaped with its upper end closed by a top cover 71 to enclose a blood flow/air removal chamber 72. A tangential blood inlet 73 is provided in one side of base member 70 and a blood outlet 74 removes a tangential and downward blood flow at the bottom of base member 70. A screen 75 is disposed within chamber 72 between blood inlet 73 and blood outlet 74 for impeding the flow of air bubbles as is known in the art. The pore size of screen 75 may be in the range of about 32 microns to about 80 microns, for example.

A toroidally-shaped float 76 is attached to the lateral struts of a brace 77 that is further attached to a stem 78. Stem 78 is captured in a support frame 79 which contains the air valve. Support frame 79 is attached to a cap 80 including the exit passage 81 of the air valve. An overflow housing section 82 is attached to top cover 71 and encloses cap 80 to produce the overflow chamber. A vacuum port 83 is provided for connecting the overflow chamber to a vacuum source.

A defoamer disc 84 is inserted on support 79 and may be disposed against cover 71. A support ring 85 is attached to base member 70 (e.g., by gluing or staking) to support a defoamer cylinder 86 at or above the maximum blood level. An air bleed-off port 87 is provided in base member 70 between blood outlet and screen 75 in order to remove bubbles that may have become entrapped below screen 75 during priming. Bleed-off port 87 may include a luer valve for manually removing air, for example.

Figure 9:
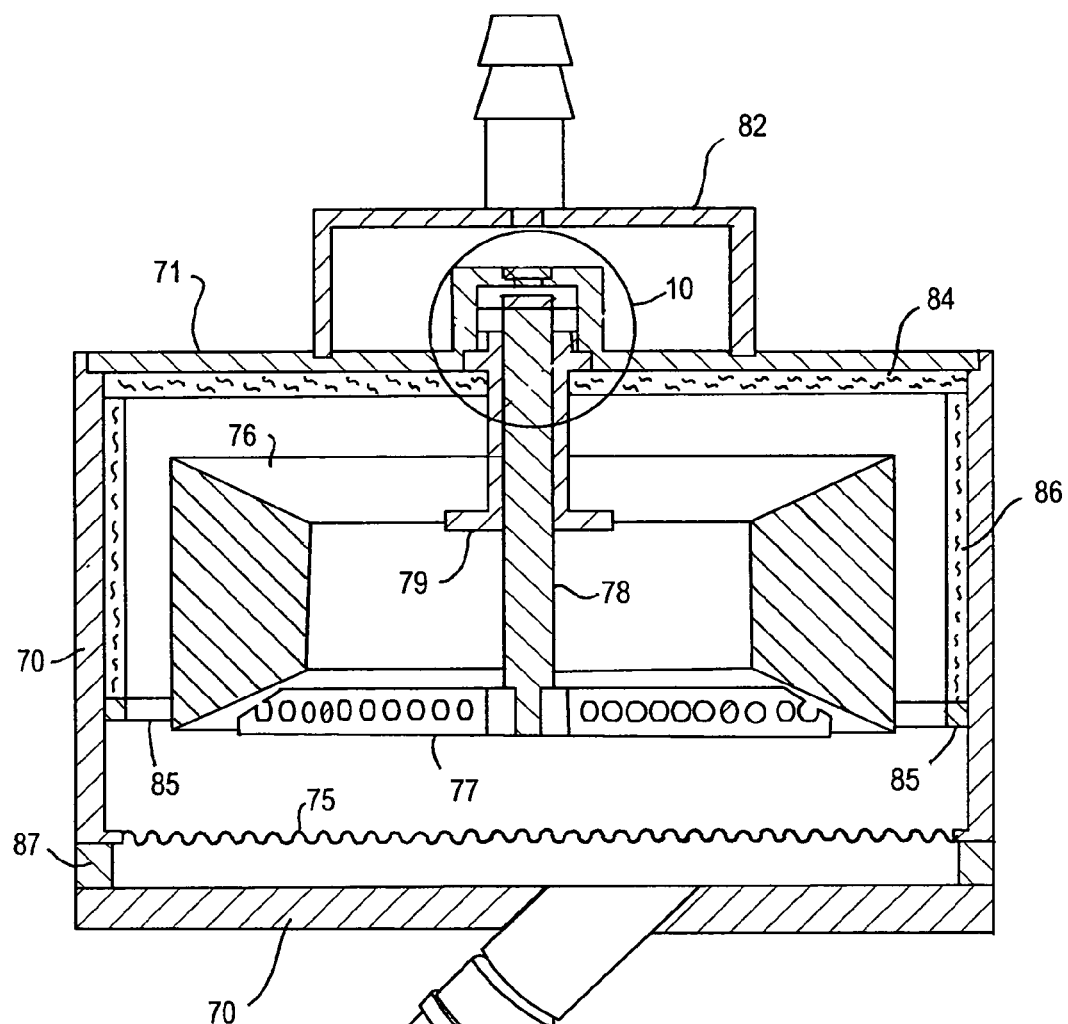
FIG. 9 is a side cross-sectional view of the device of FIG. 8.
Figure 10:
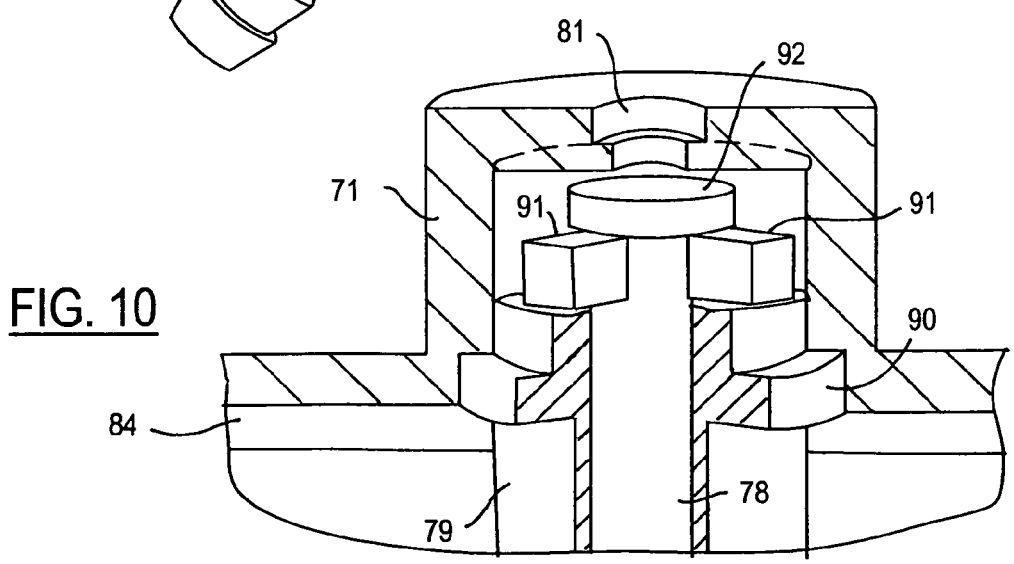
FIG. 10 is a partial cross section showing the valve components in greater detail indicated by circle 10 in FIG. 9.

FIG. 9 shows a side cross section of the device of FIG. 8 taken through the central longitudinal axis of stem 78. Thus, it can be seen that stem 78 is slidingly received by support frame 79 to selectably engage the valve elements indicated in circle 10 and which are shown in greater detail by the partial cross-sectional view of FIG. 10. Stem 78 includes a plurality of fingers 91 for aligning stem 78 within top cover 71. A plaint disk 92 is affixed to the top of stem 78 adjacent fingers 91 to selectably open and close exit passage 81 in response to the position of float 76. Support frame 79 is press fit or glued to top cover 71.

Figure 11:
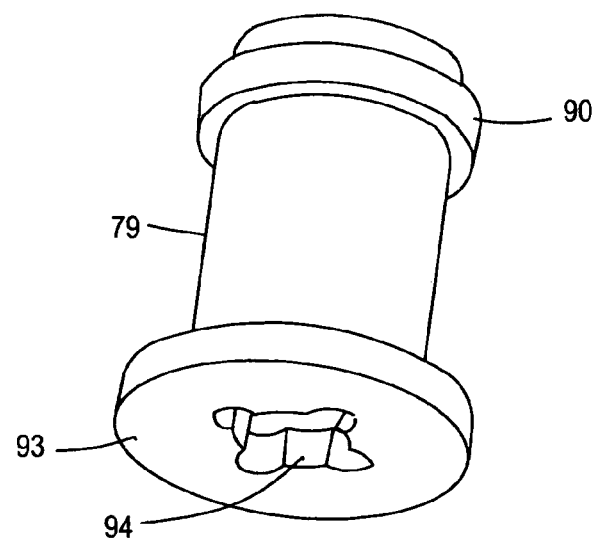
FIG. 11 is a bottom perspective view of the defoamer support and stem guide of the device of FIG. 8.

FIG. 11 shows a bottom perspective view of support frame 79. An upper collar 90 is provided for inserting into a corresponding recess in top cover 71. A bottom flange 93 includes a stem opening 94 which has an inner profile to guide stem 78 along the central longitudinal axis. In addition, several enlarged areas along the edge of opening 94 provide an air flow path toward exit passage 81.

Figure 12:
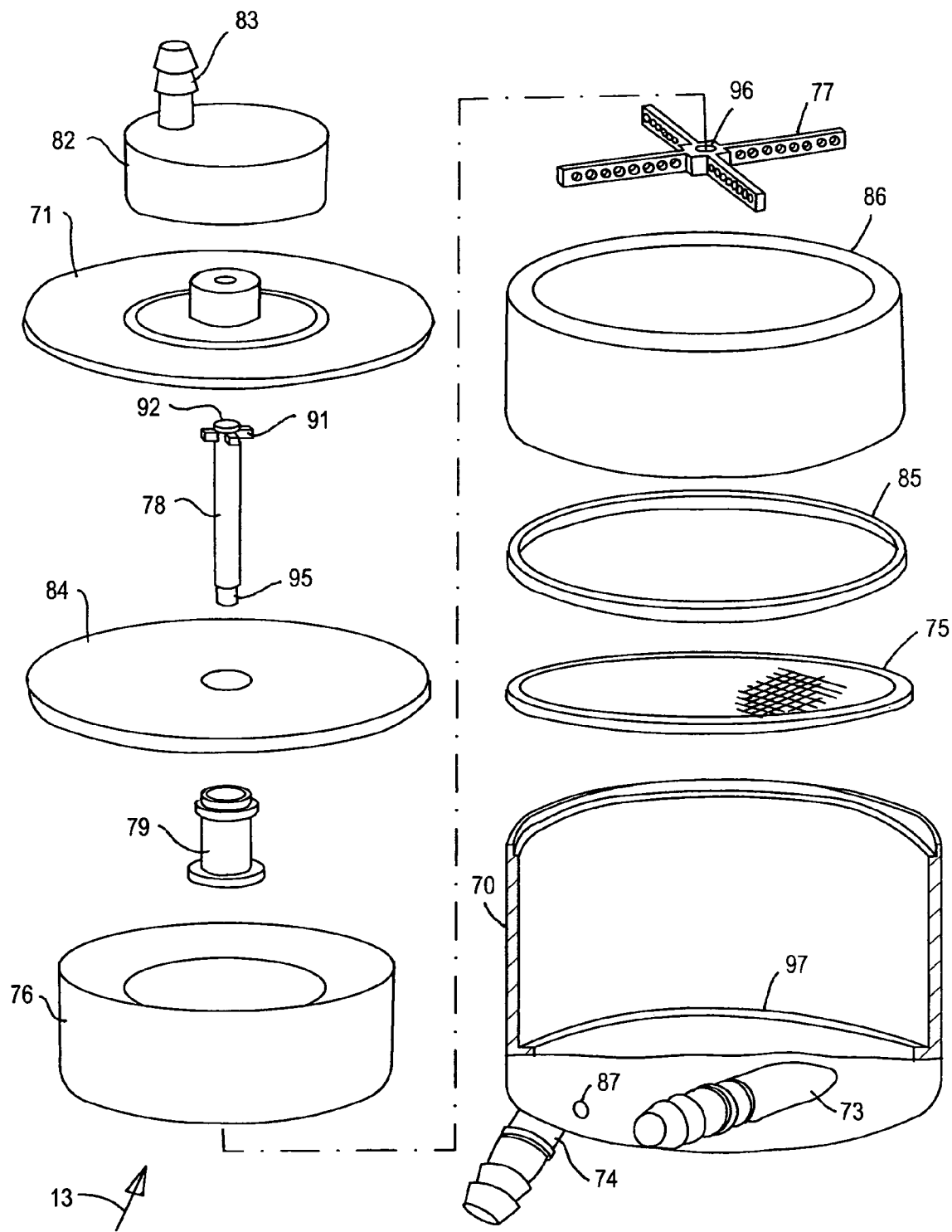
FIG. 12 is an exploded, top perspective view of the device of FIG. 8.

FIG. 12 is an exploded view of the air removal device of FIG. 8. As seen in this view, stem 78 has a cylindrical end section 95 that is fixedly mounted to a hole 96 in brace 77 by press fit, gluing, or heat staking, for example. A ledge 97 is shown in base member 70 for receiving screen 75 between the level of inlet 73 and outlet 74.

Figure 13:
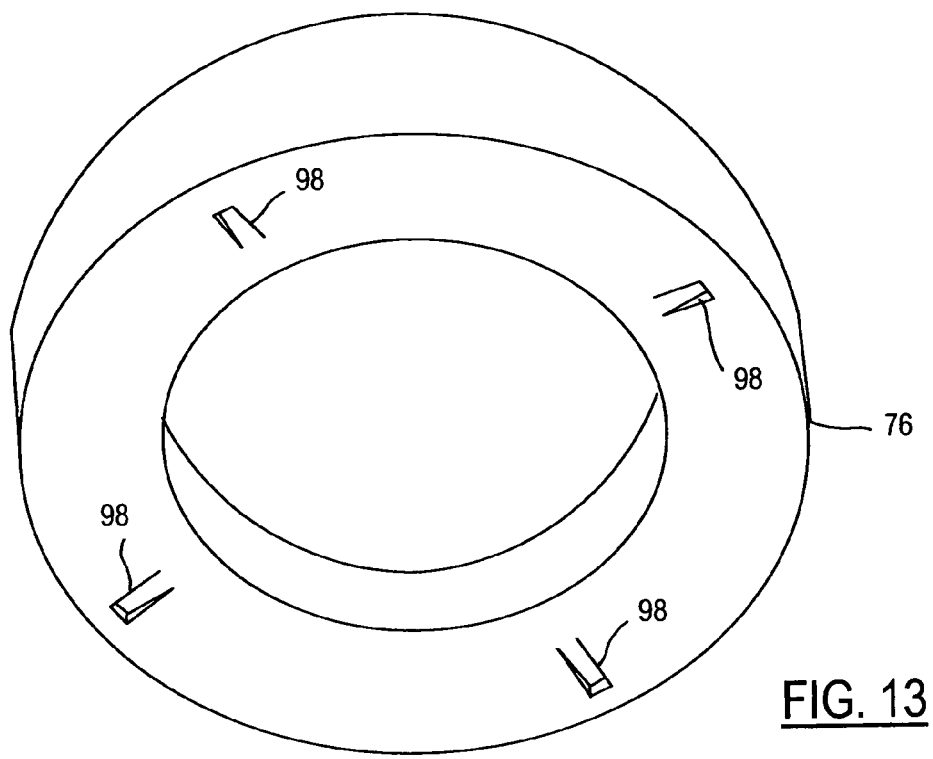
FIG. 13 is a bottom, perspective view of the float.
Figure 14:
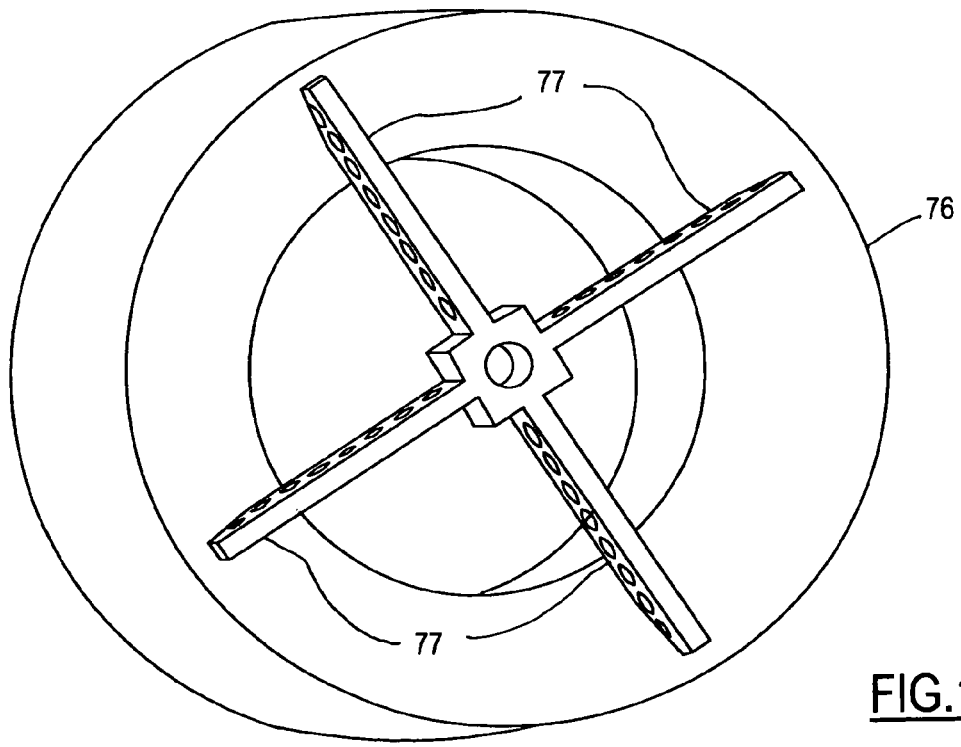
FIG. 14 is a bottom, perspective view of the float and brace.

FIG. 13 is a bottom view of float 76 showing a plurality of notches 98. As shown in FIG. 14, respective struts of brace 77 are mounted into notches 98 (e.g., by gluing) in order to fixedly attach the two.

Figure 15:
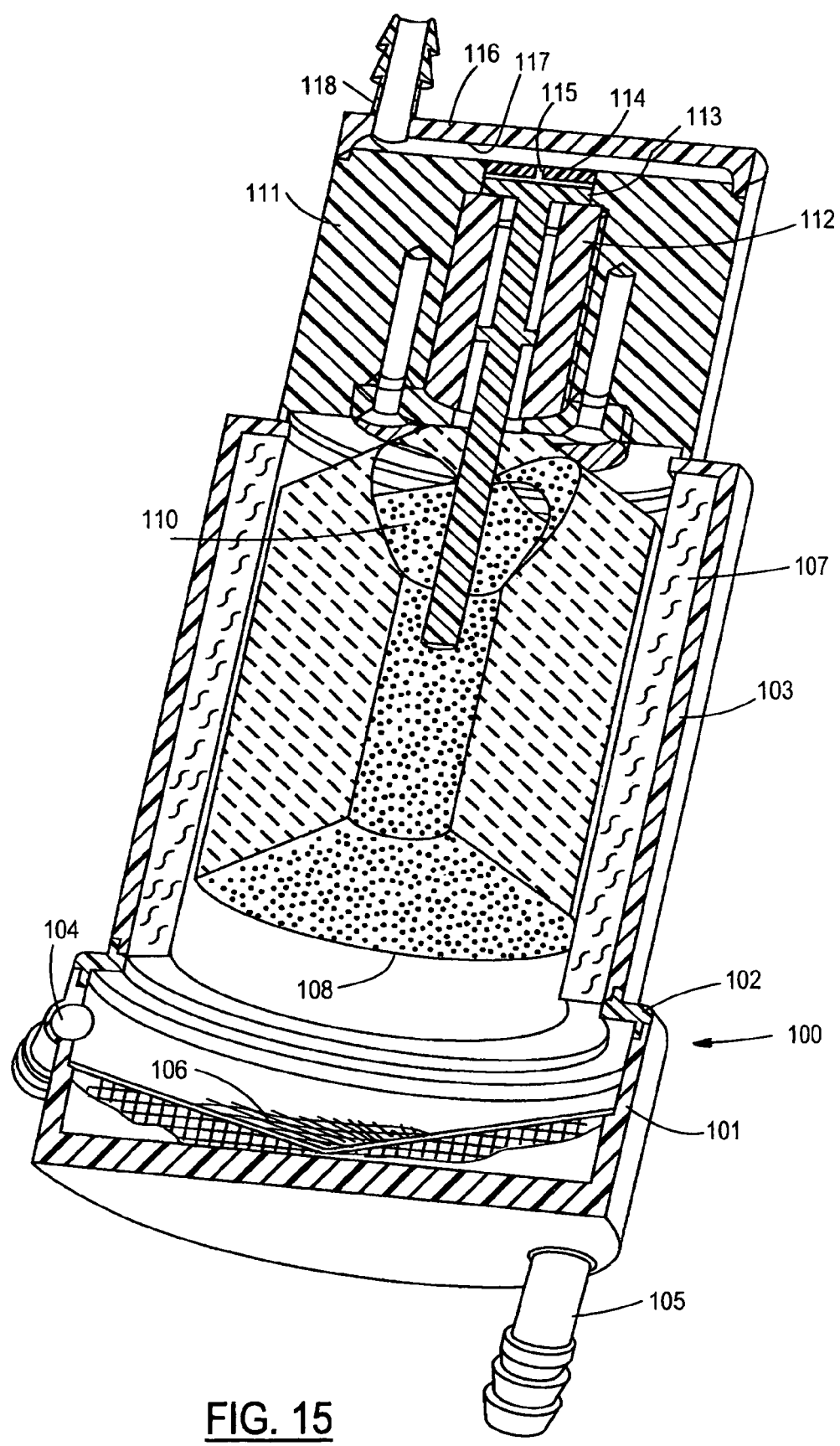
FIG. 15 is bottom perspective, cross-sectional view of an alternative embodiment of the air removal device of the present invention.

FIG. 15 shows an alternative embodiment of an air removal device 100. A rigid housing includes a lower cup-shaped section 101, a coupling section 102, and an upper cylindrical section 103. Section 101 includes a tangential inlet 104 and a tangential output 105. A conically-shaped screen 106 is disposed across lower section 101 at a height intermediate of inlet 104 and outlet 105. A defoamer cylinder 107 is attached to the inner surface of section 103. A float 108 is mounted for reciprocal movement interiorly of defoamer 107 to a stem 110.

An upper housing block 111 includes an internal bore for receiving a sleeve insert 112. Stem 110 is captured within insert 112 by its attachment to float 108 at one end and by an integral disk 113 at the other end. Disk 113 provides a sealing surface that engages a valve seat 114 fixed to a central opening of block 111 and having a central exit passage 115. Passage 115 is closed when float 108 is at is uppermost position.

A lid 116 is joined around its periphery to housing block 111 and forms a vacuum chamber 117. A vacuum port 118 couples chamber 117 to an external vacuum source (not shown). Air removal device 100 operates in the same manner as the previously described embodiments.

The float valve of the present invention can be used with types of chambers other than cylindrical and other than with a centrifugal blood flow. Any chamber which collects air, such as a box-shaped chamber with a screen or screens disposed between the blood inlet and blood outlet, can utilize the float valve for controlled release of the air. The air removal device removes air from blood in a perfusion system according to a method wherein an input blood supply is pumped through a chamber. A centrifugal flow of the input blood supply may be formed in a bottom region of the chamber to cause air to migrate toward an axial center of the chamber. A float is buoyantly suspended on the centrifugal flow wherein the float is disposed for vertical movement in the chamber, and wherein the float has an effective density less than the density of the blood. When a volume of air present within the chamber is less than a predetermined volume, then the float closes a valve at an air outlet from the chamber. When a volume of air present within the chamber is greater than the predetermined volume, then the float opens the valve to remove air from the chamber.

Preferably, the air outlet is attached to a vacuum source to quickly purge the excess air from the chamber. The air drawn from the valve may optionally be passed through a hydrophobic membrane to prevent blood from passing to the vacuum source. Blood foam that collects in the vicinity of the float is preferably contacted by blood defoamer so that bubbles are broken up and the resulting air removed and the blood returned to the circuit.

In preparing the air removal device for use in surgery, the chamber is primed with a priming fluid prior to introducing the input blood supply. Any air trapped in the bottom region of the chamber against the screen is removed through an air bleed-off port prior to introducing the input blood supply.

What is claimed is:

1. An air removal device for removing air from blood flowing in a perfusion system, comprising:
   a chamber comprised of a substantially rigid shell of a biocompatible material and having a blood flow region at a lower end thereof and having an air collection region at an upper end thereof, said chamber further having an inlet, a blood outlet, and an air outlet vertically higher than said inlet, wherein said air outlet includes an outlet mating surface proximate to an exit passage, and wherein a portion of said chamber disposed around said blood flow region is generally cylindrical about a vertical axis to provide a centrifugal flow of said blood that causes air within said blood to migrate toward said vertical axis; and
   a float disposed for vertical movement in said chamber along said vertical axis, wherein said float has an effective density less than the density of said blood, and wherein said float includes a generally toroidally shaped body and a sealing surface for engaging said outlet mating surface and blocking said exit passage when said float is at its vertically highest position.

2. The air removal device of claim 1 wherein said air outlet further includes a vacuum port for connecting to a vacuum source to withdraw air from said air collection region when said float is below said vertically highest position.

3. The air removal device of claim 2 wherein said air outlet further includes a blood overflow collection chamber between said exit passage and said vacuum port.

4. The air removal device of claim 2 further comprising a hydrophobic membrane associated with said vacuum port for preventing the passage of liquids out of said vacuum port.

5. The air removal device of claim 1 further comprising:
   a screen disposed in said chamber between said inlet and said blood outlet and having a pore size for blocking flow of air bubbles larger than a predetermined size.

6. The air removal device of claim 5 further comprising:
   an air bleed-off port coupled to said blood flow region for withdrawing air trapped in said blood flow region by said screen.

7. The air removal device of claim 1 wherein said blood outlet is vertically lower than said inlet.

8. The air removal device of claim 7 wherein said inlet is oriented substantially tangentially so that blood swirls within said blood flow region to cause said air to preferentially move to said vertical axis.

9. The air removal device of claim 7 wherein said blood outlet is oriented substantially tangentially so that blood swirls within said blood flow region to cause said air to preferentially move to said vertical axis.

10. The air removal device of claim 1 further comprising:
    a blood defoamer disposed in said air collection region.

11. The air removal device of claim 10 wherein said blood defoamer is fixedly mounted to said chamber.

12. The air removal device of claim 10 wherein said blood defoamer is mounted to said float.

13. The air removal device of claim 1 wherein said float further includes a plurality of substantially vertically-oriented channels for passing air above said float.

14. The air removal device of claim 1 wherein said toroidally shaped body includes a sloped bottom surface for preventing air accumulation beneath said float.

15. The air removal device of claim 1 wherein said float comprises a stem extending upward from a body, and wherein said sealing surface is provided on said stem.

16. The air removal device of claim 15 wherein said chamber further includes a guide surface slidably receiving said stem to align said sealing surface with said outlet mating surface.

17. The air removal device of claim 15 wherein said sealing surface comprises a pliant sheet.

18. A method of separating air from blood in a perfusion system coupled to a patient, said method comprising the steps of:

pumping an input blood supply through a chamber of a substantially rigid shell formed of a biocompatible material;

forming a centrifugal blood flow of said input blood supply in a bottom region of said chamber that is generally cylindrical about a vertical axis to cause air to leave said blood and migrate upward in said chamber;

buoyantly suspending a float on said blood flow, wherein said float is disposed for vertical movement in said chamber along said vertical axis, wherein said float includes a generally toroidally shaped body, and wherein said float has an effective density less than the density of said blood;

when a volume of air present within said chamber is less than a predetermined volume, then said float closing a valve at an air outlet from said chamber as a result of a sealing surface of said float engaging an outlet mating surface of said air outlet to block said air outlet; and when a volume of air present within said chamber is greater than said predetermined volume, then said float opening said valve to remove air from said chamber.

19. The method of claim 18 further comprising the step of: coupling a vacuum source to an output side of said valve.

20. The method of claim 19 further comprising the step of: passing air drawn from said valve through a hydrophobic membrane to prevent blood from passing to said vacuum source.

21. The method of claim 18 further comprising the step of: passing said blood flow through a screen having a pore size for blocking flow of air bubbles larger than a predetermined size.

22. The method of claim 21 further comprising the steps of: priming said chamber with a priming fluid prior to introducing said input blood supply; and removing air trapped in said bottom region against said screen through an air bleed-off port prior to introducing said input blood supply.

23. The method of claim 18 further comprising the step of: contacting blood foam rising above said blood flow with a defoamer.

\* \* \* \* \*